(12) United States Patent
Laumer et al.

(10) Patent No.: US 9,403,330 B2
(45) Date of Patent: *Aug. 2, 2016

(54) APPARATUS FOR THE PROCESSING OF PLASTICS MATERIAL CONTAINERS, BEVERAGE FILLING PLANT AND/OR BEVERAGE CONTAINER PRODUCTION PLANT AND METHOD OF SHAPING PLASTICS MATERIAL PRE-FORMS AS WELL AS USE OF HEATING PATH CONVEYING MEANS

(71) Applicant: KRONES AG, Neutraubling (DE)

(72) Inventors: Roland Laumer, Regensburg (DE); Josef Knott, Walkenstetten/Schierling (DE); Jochen Krueger, Hagelstadt (DE); Hans Scheuren, Regensburg (DE)

(73) Assignee: KRONES AG (DE)

( * ) Notice: Subject to any disclaimer, the term of this patent is extended or adjusted under 35 U.S.C. 154(b) by 436 days.

This patent is subject to a terminal disclaimer.

(21) Appl. No.: 13/712,564

(22) Filed: Dec. 12, 2012

(65) Prior Publication Data

US 2013/0154164 A1 Jun. 20, 2013

(30) Foreign Application Priority Data

Dec. 14, 2011 (DE) .......................... 10 2011 056 437

(51) Int. Cl.
*B29D 22/00* (2006.01)
*B29C 49/42* (2006.01)
(Continued)

(52) U.S. Cl.
CPC ............... *B29D 22/003* (2013.01); *A61L 2/087* (2013.01); *A61L 2/10* (2013.01); *A61L 2/208* (2013.01);
(Continued)

(58) Field of Classification Search
None
See application file for complete search history.

(56) References Cited

U.S. PATENT DOCUMENTS

| 4,313,720 A | * | 2/1982 | Spurr | ................... B29C 49/4205 264/535 |
| 6,428,735 B1 | * | 8/2002 | Deemer et al. | ................. 264/454 |

(Continued)

FOREIGN PATENT DOCUMENTS

| CN | 101528271 | 9/2009 | ................ A61L 2/04 |
| DE | 10 2008 030 156 | 12/2009 | ................ A61L 2/08 |

(Continued)

OTHER PUBLICATIONS

German Search Report issued in corresponding German Patent Application 10 2011 056 437.3, dated May 22, 2012 (5 pgs.).

(Continued)

*Primary Examiner* — Monica Huson
(74) *Attorney, Agent, or Firm* — Hayes Soloway P.C.

(57) ABSTRACT

An apparatus for the processing of plastics material containers with a shaping device for the shaping plastics material pre-forms into containers, with a heating device comprising a heating path for heating the plastics material pre-forms and with a sterilization device for the sterilization of the plastics material pre-forms, in which the sterilization device comprises a supply device to supply the plastics material pre-forms to the sterilization device, and in which the sterilization device comprises both an external disinfecting unit to sterilize the plastics material pre-forms at least on their external wall surfaces and an internal disinfecting unit to sterilize the plastics material pre-forms on their internal wall surfaces, wherein the supply device comprises heating path conveyor for conveying the plastics material pre-forms along the heating path to supply the plastics material pre-forms at least to the external disinfecting unit.

26 Claims, 1 Drawing Sheet

(51) Int. Cl.
*B29C 49/64* (2006.01)
*B29C 49/68* (2006.01)
*A61L 2/08* (2006.01)
*A61L 2/10* (2006.01)
*A61L 2/20* (2006.01)
*B29C 49/06* (2006.01)

(52) U.S. Cl.
CPC ......... *B29C 49/4205* (2013.01); *B29C 49/4252* (2013.01); *B29C 49/6418* (2013.01); *B29C 49/68* (2013.01); *A61L 2202/23* (2013.01); *B29C 49/06* (2013.01)

(56) References Cited

U.S. PATENT DOCUMENTS

| | | | |
|---|---|---|---|
| 8,083,512 B2 | 12/2011 | Adriansens | 425/174.4 |
| 2003/0165400 A1 | 9/2003 | Hayakawa et al. | 422/28 |
| 2008/0260887 A1* | 10/2008 | Adriansens | B29C 49/46 425/524 |
| 2009/0317506 A1 | 12/2009 | Adriansens | 425/103 |
| 2010/0047120 A1 | 2/2010 | Adriansens et al. | 422/22 |
| 2010/0089009 A1 | 4/2010 | Till | 53/452 |
| 2011/0061343 A1* | 3/2011 | Roithmeier et al. | 53/452 |
| 2011/0225932 A1 | 9/2011 | Hirdina | 53/426 |

FOREIGN PATENT DOCUMENTS

| | | | |
|---|---|---|---|
| DE | 10 2007 017 938 | 1/2010 | B29C 49/42 |
| EP | 2366657 | 9/2011 | B67C 3/04 |
| EP | 2388129 | 11/2011 | B29C 49/46 |

OTHER PUBLICATIONS

European Office Action (no translation) issued in related application No. 12197240.0, dated Mar. 18, 2013 (6 pgs).

Chinese Office Action issued in related application No. 201210546362.1, dated Aug. 27, 2014 (2 pgs).

* cited by examiner

U.S. Patent      Aug. 2, 2016      US 9,403,330 B2
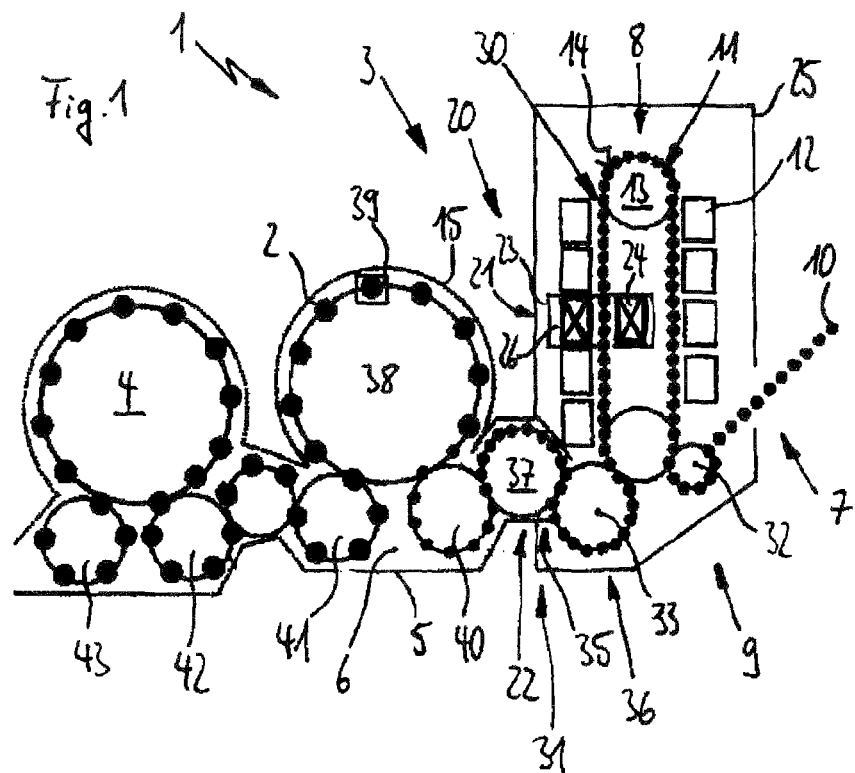
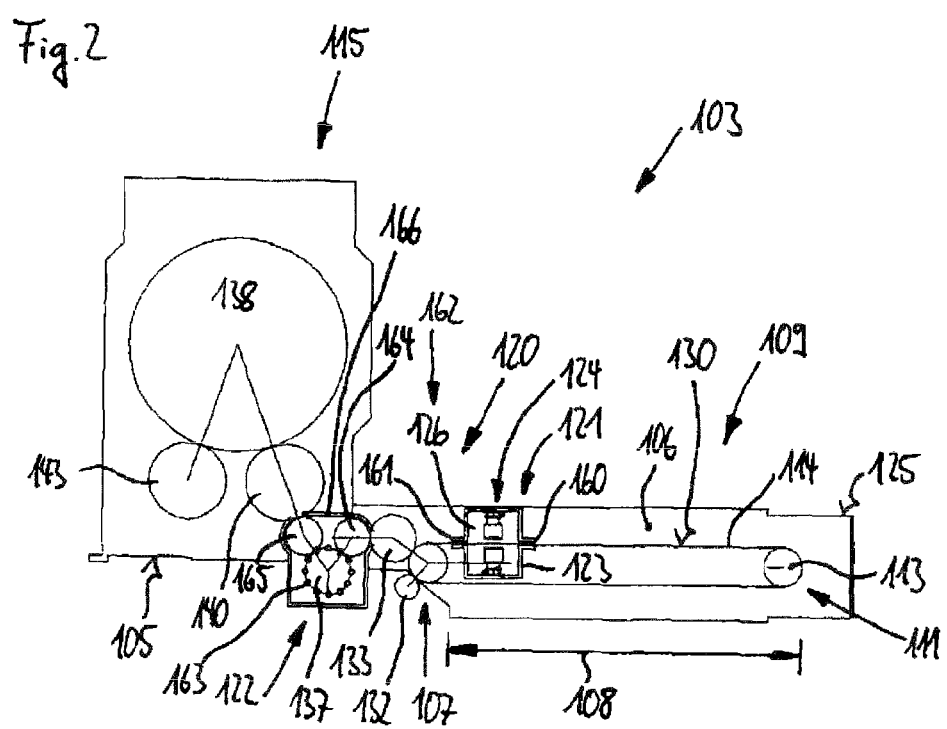

APPARATUS FOR THE PROCESSING OF PLASTICS MATERIAL CONTAINERS, BEVERAGE FILLING PLANT AND/OR BEVERAGE CONTAINER PRODUCTION PLANT AND METHOD OF SHAPING PLASTICS MATERIAL PRE-FORMS AS WELL AS USE OF HEATING PATH CONVEYING MEANS

BACKGROUND OF THE INVENTION

The invention relates to an apparatus for the processing of plastics material containers, with a shaping device for shaping plastics material pre-forms into the plastics material containers, with a heating device comprising a heating path for heating the plastics material pre-forms and with a sterilization device for the sterilization of the plastics material pre-forms, in which the sterilization device comprises a supply device in order to supply the plastics material pre-forms to the sterilization device, and in which the sterilization device can comprise or has respectively both an external disinfecting unit in order to sterilize the plastics material pre-forms at least on the external wall surfaces thereof and an internal disinfecting unit in order to sterilize the plastics material pre-forms on the internal wall surfaces thereof.

In addition, the invention relates to a beverage filling plant and/or a beverage container production plant with an apparatus for the processing of plastics material containers. The plastics material containers are, in particular, plastics material pre-forms, but an application to other plastics material containers, such as in particular plastic bottles, would also be possible.

The invention also relates to a method of shaping plastics material pre-forms into plastics material containers, in which the plastics material pre-forms are expanded by means of a gaseous medium, and in particular compressed air, to form the plastics material containers, in which the plastics material pre-forms are pre-heated along a heating path of a heating device before the expansion, and in which the plastics material pre-forms are conveyed along the heating path by means of heating path conveying means from a heating path supply device to a heating path removal device.

Furthermore, the invention relates to the use of heating path conveying means by which plastics material pre-forms are moved along the heating path of a heating device in order to heat the plastics material pre-forms.

Generic apparatus for the processing of plastics material containers with a shaping device for shaping plastics material pre-forms into the plastics material containers are well known from the prior art.

As well as the actual shaping and a filling which follows immediately or subsequently, the sterilization of a plastics material container to be subsequently filled with beverages is one of the central process steps in an apparatus for the processing of plastics material containers which operates aseptically at least in part. The possibilities of sterilization which are employed in this case can vary in particular with respect to the disinfectants which can be used and the respective performance of the process. To begin with, use was made almost exclusively of chemical disinfectants in which a germ-destroying effect is produced on the basis of chemical processes. More recent developments differ from this in that they use an ionized radiation in order to achieve at least an adequate reduction in germs on the plastics material container in question or on a plastics material pre-form out of which the plastics material container is produced. This ionized radiation consists in most applications of accelerated electrons which are produced by a suitable radiation source and which are accelerated onto and/or into the plastics material container to be sterilized or the plastics material pre-form to be sterilized respectively. A major advantage of sterilization by means of ionized radiation lies in the reduction or ideally in the complete avoidance of the use of chemical disinfectants.

Current sterilization systems available on the market at present have for example an internal disinfecting unit which comprises on the one hand an electron producing device for producing and accelerating the electrons and on the other hand a radiation finger element for guiding the electrons on internal wall surfaces of plastics material containers or plastics material pre-forms in order to be able to disinfect the internal wall surfaces through an opening in the respective plastics material containers or plastics material pre-forms. Other sterilization systems have electron producing devices by means of which specifically only external wall regions can be disinfected. In addition, there are also electron producing devices by means of which internal wall surfaces can be processed from the outside through wall regions of the plastics material containers or plastics material pre-forms respectively.

Before the plastics material pre-forms can be subjected to the actual expansion process, they have to be not only conveyed inside the respective processing device arranged upstream but also transferred between the individual processing devices, as a result of which a multiplicity of conveying, supplying and transferring devices are required. By way of example, a plastics material pre-form is first supplied to a heating device by means of a supply device, and there it is moved by means of a conveying device along a heating path past heating elements for heating in order to be subsequently transferred to a sterilization device by means of a transfer device. At the sterilization device the plastics material pre-form is processed by means of another conveying device ideally on an internal disinfecting unit and subsequently on an external disinfecting unit or vice versa, before it is transferred to a shaping device by means of a further transfer device. The plastics material pre-form must frequently be gripped several times by various gripping systems or the like, supplied, transferred, conveyed and/or removed in order to be able to convey it to the position necessary for the respective processing. It is to be understood that on account of the quite high structural outlay not only a more time-intensive conveying but also an increased maintenance outlay are involved on a multiple-component apparatus of this type for the processing of plastics material containers.

By way of example, the Offenlegungsschrift [Laid-Open Specification] DE 10 2008 030 156 A1 discloses a generic apparatus of this type and a related method of producing plastics material containers. The apparatus has a shaping device by means of which plastics material pre-forms are shaped into the plastics material containers. The plastics material containers can then be filled, in particular, with germ-sensitive beverages in a filling device arranged downstream, so that a sterilization device for the sterilization of the plastics material containers is arranged between the shaping device and the filling device, in order to reduce the risk of contaminated plastics material containers being filled and the beverages becoming undrinkable as a result. In order to be able to carry out the actual shaping process more advantageously, the plastics material pre-forms are preheated in advance in a heating device. In this case it is further provided that the plastics material pre-forms are already sterilized upstream of the shaping device in order to be able to ensure a greater certainty of disinfection as a whole. In this respect, it is proposed in the Offenlegungsschrift DE 10 2008 030 156

A1 that a first sterilization device should already be provided upstream of the heating device. In this context it is pointed out that this first sterilization device or a further sterilization device can be arranged inside the heating device. In addition, for example, a sterilization device can be arranged upstream of the heating device, a further one in the heating device and a further one downstream of the heating device and upstream of the shaping device.

The object of the invention is further to develop generic apparatus in such a way that their structural design is simpler, in particular with respect to a sterilization device for the sterilization of plastics material pre-forms.

SUMMARY OF INVENTION

The object of the invention is attained by an apparatus for the processing of plastics material containers with a shaping device for the shaping of plastics material pre-forms into the plastics material containers, with a heating device comprising a heating path for heating the plastics material pre-forms and with a sterilization device for the sterilization of the plastics material pre-forms, in which the sterilization device comprises a supply device in order to supply the plastics material pre-forms to the sterilization device, and in which the sterilization device can comprise or has respectively both an external disinfecting unit in order to sterilize the plastics material pre-forms at least on their external wall surfaces and an internal disinfecting unit in order to sterilize the plastics material pre-forms on their internal wall surfaces, the apparatus being characterized in that the supply device comprises heating path conveying means for conveying the plastics material pre-forms along the heating path, in order to supply the plastics material pre-forms at least to the external disinfecting unit.

In an advantageous manner the structural outlay of the present apparatus is considerably simplified by the fact that the supply device comprises heating path conveying means for conveying the plastics material pre-forms along the heating path, in order to supply the plastics material pre-forms at least to the external disinfecting unit. Hitherto, each part of a generic apparatus for the processing of plastics material containers had separate conveying means, in particular for the conveying of the plastics material pre-forms, as a result of which the apparatus as a whole was also relatively maintenance-intensive. It is accordingly advantageous for these heating path conveying means to be same conveying means which are also used for conveying the containers through the heating device.

The object of the invention is accordingly also attained by a method of shaping plastics material pre-forms into plastics material containers, in which the plastics material pre-forms are expanded by means of a gaseous medium, and in particular by means of compressed air, to form the plastics material containers, in which before the expansion the plastics material pre-forms are pre-heated on a heating path of a heating device, and in which the plastics material pre-forms are conveyed by means of heating path conveying means along the heating path from a heating path supply device to a heating path removal device, the method being characterized in that the plastics material pre-forms are sterilized at least in part on the heating path, and the plastics material pre-forms held on holding elements of the heating path conveying means being sterilized directly on a sterilization device.

Ideally the plastics material pre-forms held on the holding elements of the heating path conveying means are supplied without a change of position with respect to the plastics material pre-form holding elements of the heating path conveying means to the sterilization device and are sterilized there.

The design of the apparatus according to the invention can advantageously be further simplified if the heating path conveying means comprise a plurality of holding elements for holding the plastics material pre-forms, in particular mandrel-type holding elements for holding the plastics material pre-forms on the inside, in which case the holding elements or the mandrel-type holding elements respectively of the heating path conveying means are capable of being arranged temporarily on the external disinfection device.

Holding elements or mandrel-type holding elements respectively have long been known from the prior art. A plastics material pre-form can be gripped and held by them in particular on its opening region on the outside and preferably on the inside, so that an advantageous individual conveying of the respective plastics material pre-form can be ensured.

A preferred variant of embodiment provides that the sterilization device is incorporated only in part inside the heating device, it being advantageous for the external disinfection unit to be arranged inside the heating path and for the internal disinfection unit to be arranged outside the heating path. In particular, known heating path conveying means are highly suitable for providing the plastics material pre-forms on an external disinfection unit, since they can hold the plastics material pre-form from the inside, so that the risk of the formation of a shadow on the external wall surface to be disinfected can be virtually eliminated.

In the sense of the invention the expression "formation of a shadow" describes that regions of the external wall surface could not be disinfected or could be only insufficiently disinfected by the sterilization device, since they are disadvantageously covered by components, such as for example holding elements for holding the plastics material pre-forms.

Depending upon the design which the present apparatus has, in terms of as great a creative freedom as possible it is advantageous for the external disinfection unit to be arranged at the start of the heating path upstream of a heating element and downstream of an inlet of the heating device, between two heating elements inside the heating path or at the end of the heating path downstream of a heating element and upstream of a transfer device at the outlet and inside the heating device.

The structural outlay of the apparatus with respect to an operationally reliable 360° disinfection of the plastics material pre-forms can be further reduced extremely well by the heating device having means for rotating the holding elements or mandrel-type holding elements, by means of which the plastics material pre-forms are capable of being arranged at least on the external disinfection device so as to be rotatable about a vertical axis during an external sterilization.

In addition, it is advantageous for the heating device to comprise a generation device for the generation of electrical charge particles, by means of which the plastics material pre-forms are capable of being sterilized. The sterilization of a plastics material pre-form can be further simplified in structural terms by a generation device incorporated in the heating device in this way. It is advantageous for the disinfection device also to have an acceleration device for accelerating the charge carriers as well as an outlet window through which the charge carriers can issue. This outlet window can be for example a titanium foil. In addition, it is also advantageous for a cooling device to be provided for cooling the outlet window, in particular a cooling device which acts upon the outlet window with a gaseous medium.

It is particularly preferred for the charge carriers to be electrons, but it would also be possible for other charge carriers to be used, such as for example protons or alpha particles.

A preferred method variant accordingly also provides that the plastics material pre-forms are irradiated at least in part with charge carriers inside the heating path for sterilization purposes.

In this case it is advantageous for the plastics material pre-forms to rotate about their longitudinal axis during the external disinfection, since a more reliable disinfection result can also be achieved in this way.

It is understood that on account of the means for rotating the holding elements or mandrel-type holding elements the apparatus can advantageously also carry out a complete external disinfection if the generation device comprises only one charge particle emitter.

It is preferable for a generation device of this type nevertheless to be provided with two charge particle emitters, a first charge particle emitter being arranged on a first side of the heating path conveying means and a second charge particle emitter being arranged on another side of the heating path conveying means opposite the first side. As a result, an external disinfection can be carried out more rapidly and/or in a manner more reliable in operation. In this case it is possible for these mutually opposed charge particle emitters to be arranged offset with respect to each other along the conveying path of the containers. It is advantageous for the conveying path of the containers to extend at least locally and preferably completely in a straight line in the region of the charge particle emitters. A course curved in the form of a circle for example would also, however, be possible.

If the heating device comprises at least in part a casing which screens off the charge particles, the sterilization device, in particular a charge generation device of the external disinfection unit, can be readily incorporated in the heating path. In addition, this screening is also used in particular for screening out the X-ray radiation which is generated by the aforesaid charge particles or the accelerated movement thereof respectively.

An aseptic processing environment which is particularly reliable in operation can already be produced on the heating device if the heating device comprises an additional clean room in which the sterilization device is arranged at least in part. It is preferable for this clean room to surround at least the conveying path of the plastics material containers.

In addition, a particularly preferred variant of embodiment provides that an internal disinfection unit of the sterilization device is arranged outside the heating device and thus at a distance from an external disinfection unit of the sterilization device arranged inside the heating device, in which case in particular both the internal disinfection unit and the external disinfection unit are arranged inside a common clean room under aseptic conditions.

In the same way it is advantageous for the heating device to have a casing inside which the external disinfection unit is arranged at least in part and at the outlet of which the internal disinfection unit is arranged outside the casing. In this way, the heating device can be made very compact and scarcely larger than before. In addition, existing heating devices can where necessary be retrofitted in a simpler manner as a result.

The object of the invention is also attained by a beverage filling plant and/or a beverage container production plant with an apparatus for shaping plastics material pre-forms into plastics material containers in accordance with one of the features described here.

In addition, the object of the invention is also attained by the use of heating path conveying means by which plastics material pre-forms are moved along the heating path of a heating device for heating the plastics material pre-forms, in order to hold the plastics material pre-forms in front of a disinfection unit of a sterilization device for the sterilization of the plastics material pre-forms.

The structural outlay for conveying the plastics material pre-forms can be kept particularly low by such a use according to the invention.

It is understood that the present invention can be advantageously applied not only to a heating device for heating plastics material pre-forms but also with respect to a heating device for plastics material containers if this is expedient.

BRIEF DESCRIPTION OF THE DRAWINGS

Further advantages, aims and properties of the present invention are explained with reference to the accompanying drawing and the following description, in which a beverage container production plant with a heating device comprising a sterilization device is illustrated and described by way of example. In the drawings:

FIG. 1 is a diagrammatic view of a first beverage container production plant for the production of plastics material containers with a sterilization device comprising a supply device and with heating path conveying means for conveying the plastics material pre-forms along a heating path of the heating device, and FIG. 2 is a diagrammatic view of a further beverage container production plant for the production of plastics material containers with a sterilization device comprising a supply device and with heating path conveying means for conveying the plastics material pre-forms along a heating path of the heating device.

DETAILED DESCRIPTION OF THE INVENTION

The beverage container production plant 1 shown by way of example in FIG. 1 for the production of plastics material containers 2 essentially has an apparatus 3 for the processing of the plastics material containers 2 and a filling device 4 attached thereto, which are accommodated in a clean room 6 in a common casing 5 of the beverage container production plant 1 under aseptic production and filling conditions.

A heating device 9, which comprises a heating path 8 and in which plastics material pre-forms 10 are heated, is provided at the inlet side 7 of the apparatus 3. In this case the plastics material pre-forms 10 are conveyed through the heating device 9 by means of a heating path conveying device 11 and are heated by a plurality of heating elements 12 during this. The heating path conveying device 11 essentially comprises two reversing units 13 (numbered only by way of example) and heating path conveying means 14, such as a circulating chain. In order to hold the individual plastics material pre-forms 10 the heating path conveying means 14 have a plurality of mandrel-type holding elements known per se (not shown), by means of which the respective plastics material pre-forms 10 can held on the inside at the later access or bottleneck region of the plastics material container 2. This holding of the plastics material pre-forms 10 on the inside makes it possible in an advantageous manner for the external wall surfaces of the plastics material pre-forms 10 not to be covered by any holding elements and thus to be accessible completely freely from the outside. It is advantageous for the plastics material pre-forms 10 to be capable of being heated by the heating elements 12 without the formation of shadows in this way.

A sterilization device 20 is provided on the heating device 9 and upstream of a shaping device 15 on which the plastics material pre-forms 10 are shaped into the plastics material containers 2. The sterilization device 20 comprises an external disinfection unit 21 and an internal disinfection unit 22 which are arranged separately from each other on the heating device 9. In this way, the actual sterilization region which should be provided with its own protection for screening out the harmful (X-ray) radiation is divided into two separate portions, in particular an external sterilization region and an internal sterilization region, these two portions being advantageously arranged upstream of the shaping device (which can be a stretch blow moulding machine for example) in the conveying region of the containers.

The external disinfection unit 21 of the sterilization device 20 is arranged directly incorporated in the heating path 8 between two heating elements 12, i.e. also therefore inside the heating device 9. It comprises an external disinfection unit casing 23 in which a generation device 24 for generating electrical charge particles is positioned, by means of which the electrical charge particles can disinfect the external wall surfaces of the plastics material pre-forms 10 under aseptic conditions.

In this respect the heating device 9 is provided with the generation device 24 for the generation of the electrical charge particles, as a result of which the external disinfection unit 21 of the sterilization device 20 can be incorporated particularly satisfactorily in the heating device 9.

In order properly to protect the environment to the necessary degree from the electrical charge particles produced and, in particular, also to screen it off from X-ray radiation which occurs, the heating device 9 has at least in part a casing 25 which screens out the charge particles.

The aseptic conditions can be specially ensured on the external disinfection unit 21 in a manner which is particularly reliable in operation if the heating device 9 also has an additional clean room 26 of the sterilization device.

The sterilization device 20 comprises a supply device 30 in order to supply the plastics material pre-forms 10 to the external disinfection unit 21, the supply device 30 of the sterilization device 20 comprising according to the invention the heating path conveying means 14 provided with the mandrel-type holding elements in order to supply the plastics material pre-forms 10 in a particularly simple manner structurally at least to the external disinfection unit 21 of the sterilization device 20. In this respect the mandrel-type holding elements of the heating path conveying means 14 are capable of being arranged temporarily on the external disinfection unit 21 (in particular by being moved past the latter). The external disinfection unit 21 is advantageously arranged in a stationary manner.

It also follows from this that the heating device 9 advantageously has means for rotating the mandrel-type holding elements, by means of which the plastics material pre-forms 10 are capable of being arranged at least on the external disinfection unit 21 so as to be rotatable about a vertical axis during an external sterilization.

In this embodiment the internal disinfection unit 22 of the sterilization device 20 is arranged at the outlet 31 of the heating device 9.

In this respect the sterilization device 20 is incorporated inside the heating device 9 only in part, the external disinfection unit 21 being arranged inside the heating path 8 and the internal disinfection unit 22 being arranged outside the heating path 8.

In this respect a method of shaping the plastics material pre-forms 10 into the plastics material containers 2 can be advantageously implemented in particular with the present apparatus 3, in which method the plastics material pre-forms 10 are expanded by means of compressed air to form the plastics material containers 2, in which before the expansion the plastics material pre-forms 10 are pre-heated on the heating path 8 of the heating device 9, and in which the plastics material pre-forms 10 are conveyed by means of the heating path conveying means 14 along the heating path 8 from a heating path supply device 32 to a heating path removal device 33, the plastics material pre-forms 10 being sterilized at least in part on the heating path 8, and the plastics material pre-forms 10 held on holding elements 12 of the heating path conveying means 14 being sterilized directly on the sterilization device 20.

The heating path removal device 33 constitutes a transfer unit 36 which transfers the plastics material pre-forms 10 to the internal disinfection unit 22 of the sterilization device 20. This sterilization device 20 has a conveying wheel 37 and sterilization elements (not shown here) can be arranged on this conveying wheel 37 or even in a stationary manner. Sterilization by hydrogen peroxide gas or even, as mentioned above with respect to the external disinfection unit 21, by charge carriers, in particular electrons, electromagnetic radiation or UV radiation or the like and/or combinations of these, is possible for example in this region. In particular, however, the internal sterilization of the plastics material pre-forms 10 is carried out in this region.

The reference number 6 designates in its entirety a clean room, the external boundaries of which are indicated by the common casing 5. In a further preferred embodiment the clean room 6 is not only arranged in the region of a conveying wheel 38 of the shaping device 15 and the filling device 4, but it already starts if possible in the region of the heating device 9, the sterilization device 20, the supply of the plastics material pre-forms and/or the production of the plastics material pre-forms. The clean room 6 is adapted to the external shape of the individual components of the plant. In this way the volume of the clean room 6 can be reduced.

The reference number 15 designates in its entirety a shaping device, in which a plurality of blow moulding stations 39 are arranged on the conveying wheel 38, only one of these blow moulding stations 39 being shown here. The plastics material pre-forms 10 are expanded by these blow moulding stations 39 to form the plastics material containers 2.

The reference number 40 relates to a supply wheel device which transfers the plastics material pre-forms 10 to the shaping device 15, and the reference number 41 relates to a removal wheel device which removes the produced plastics material containers 2 from the shaping apparatus 15. It will be seen that in the region of the supply device 40 and the removal device 41 the clean room 6 has recesses in each case which receive these devices 40, 41. In this way, a transfer of the plastics material pre-forms 10 to the shaping apparatus 15 or a transfer of the plastics material containers 2 from the shaping apparatus 15 can be achieved in a particularly advantageous manner.

The expanded plastics material containers 2 are transferred to the filling device 4 by a transfer unit 42 and they are then removed from this filling device 4 by way of a further conveying unit 43. In this case the filling device 4 is also situated inside the aforesaid clean room 6, as already described. In the case of the filling device 4 it would also be possible for the entire filling device 4 with for example a reservoir for a beverage not to be arranged completely inside the clean room 6, but also in this case only those areas in which the plastics material containers 2 are in fact guided. In this respect, it would also be possible for the filling device 4 to be designed in a similar manner to the shaping apparatus 15 for shaping the shaping plastics material pre-forms 10. The individual conveying and transfer devices respectively are preferably conveying star wheels.

In the case of the further embodiment shown in FIG. 2, another apparatus 103 for the processing of plastics material containers (not shown here) is designed essentially with a shaping device 115 for shaping plastics material pre-forms (not shown here) into the plastics material containers (not shown), with a heating device 109 comprising a heating path 108 for heating the plastics material pre-forms and with a sterilization device 120 for sterilizing the plastics material pre-forms.

The sterilization device 120 is formed from an external disinfection unit 121 and an internal disinfection unit 122, the external disinfection unit 121 having a supply device 130 in order to supply the plastics material pre-forms to the sterilization device 120, which is characterized according to the invention by heating path conveying means 114 of a heating path conveying device 111 of the heating device 109 for conveying the plastics material pre-forms along the heating path 108, in order to supply the plastics material pre-forms in an extremely simple manner structurally at least to the external disinfection unit 121 in this way.

The external disinfection unit 121 is situated in a clean room 106 which is enclosed in its entirety by a common casing 105 of the apparatus 103. In addition, the external disinfection unit 121 has a clean room 126 of the sterilization device which is additionally surrounded by a casing 123 of the external disinfection unit and in which a generation device 124 for the generation of electrical charge particles is accommodated. The casing 123 of the external disinfection unit forms a screening device with respect to the charge particles and/or with respect to X-ray radiation which may occur.

The heating path conveying means 114 are guided through this sterilization device clean room 126, so that plastics material pre-forms held on it can be sterilized directly on the external disinfection unit 120 in an advantageous manner, as has already been explained with respect to the first embodiment.

In this respect, in this second embodiment too the heating path conveying means 114 directly form a supply device 130 of the sterilization device 120 at least with respect to its external disinfection unit 121.

In order to guide the heating path conveying means 114 through the external disinfection unit 120, the external disinfection unit 120 has an inlet opening 160 and an outlet opening 161, which are both situated inside a heating casing 125 of the heating device 109.

In an advantageous manner the plastics material pre-forms are held on the inside by mandrel-type holding elements, so that they can also be satisfactorily disinfected on the outside at the external disinfection unit 120.

In this case the external disinfection unit 120 is positioned at the end 162 of the heating path 108 and upstream of a heating path removal device 133. In addition, the external disinfection device 120 is mounted between two reversing units 113 for reversing the heating path conveying means 114, one of the reversing units 113 interacting directly on the inlet side 107 of the heating device 109 both with a heating path supply device 132 and with a heating path removal device 133.

The internal disinfection unit 122 of the sterilization device 120 is positioned functionally between the heating path removal device 133 and a supply wheel device 140 and it has a conveying wheel 137 and internal sterilization elements known per se with radiation finger elements 163, by means of which the internal wall surfaces of the plastics material pre-forms can be disinfected. The conveying wheel 137 communicates with two transfer star wheel devices 164 and 165, by means of which the plastics material pre-forms are introduced into the internal disinfection unit 122 or separated out of the internal disinfection unit 122 respectively. The conveying wheel 137, the radiation finger elements 163 and the transfer star wheel devices 164, 165 are arranged additionally protected in this case in an internal disinfection unit casing 166. The internal disinfection unit casing 166 at the same time forms a screening device with respect to the charge particles and/or with respect to X-ray radiation.

It is preferable for the containers to be moved in a longitudinal direction of the containers with respect to the radiation finger elements 163, in order to introduce the radiation finger elements—at the lower ends of which outlet windows for the electrons are preferably provided—into the containers. In this case it is preferred for the containers to be moved in the longitudinal direction thereof, but it would also be possible for the radiation finger elements 163 to be moved or even both the radiation finger elements and the containers to be moved.

The two partial areas described here for the external and internal disinfection of the pre-forms are preferably part of the aseptic housing of the plant as a whole and they should preferably be designed with a view to hygienic considerations. It is therefore preferable for at least one partial area of the heating apparatus likewise to be designed with a view to hygienic considerations. Conventional housings can be used between the two disinfection regions since the radiation has to be screened off only indirectly in each case at the emitters.

The plastics material pre-forms sterilized in this way and supplied to a blow moulding wheel 138 by means of the supply wheel device 140 are expanded at the shaping device 115 to form the plastics material containers, before they are then made ready for further use at a conveying unit 143.

It is to be understood that the embodiments explained above are only first designs of the apparatus according to the invention for the processing of plastics material containers. In this respect the designs of the invention are not restricted to these embodiments.

The Applicants reserve the right to claim all the features disclosed in the application documents as being essential to the invention, insofar as they are novel either individually or in combination as compared with the prior art.

LIST OF REFERENCES 1 beverage container production plant
2 plastics material containers
3 apparatus for the processing
4 filing device
5 common casing
6 clean room
7 inlet side
8 heating path
9 heating device
10 plastics material pre-forms
11 heating path conveying device
12 heating elements
13 reversing elements
14 heating path conveying means 15 shaping device
20 sterilization device
21 external disinfection unit
22 internal disinfection unit
23 external disinfection unit casing
24 generation device
25 heating device casing
26 heating device clean room
30 supply device
31 outlet
32 heating path supply device
33 heating path removal device
36 transfer unit
37 conveying wheel
38 blow moulding wheel
39 blow moulding stations
40 supply wheel device
41 removal wheel device
42 transfer unit
43 conveying unit
103 apparatus for the processing
105 common casing
106 clean room
107 inlet side
108 heating path
109 heating device
111 heating path conveying device
113 reversing units
114 heating path conveying means
115 shaping device
120 sterilization device
121 external disinfection unit
122 internal disinfection unit
123 external disinfection unit casing
124 generation device
125 heating device casing
126 sterilization device clean room
130 supply device
132 heating path supply device
133 heating path removal device
137 conveying wheel
138 blow moulding wheel
140 supply wheel device
143 conveying unit
160 inlet opening
161 outlet opening
162 end
163 radiation finger elements
164 first transfer star wheel device
165 second transfer star wheel device
166 internal disinfection unit casing

The invention claimed is:

1. An apparatus for processing plastics material containers comprising a shaping device for shaping plastics material pre-forms into plastics material containers, a heating device comprising a heating path for heating the plastics material pre-forms and with a sterilization device for the sterilization of the plastics material pre-forms, in which the apparatus comprises a supply device for supplying the plastics material pre-forms to the sterilization device, wherein the sterilization device comprises both a dedicated external disinfecting unit for sterilizing the plastics material pre-forms at least on their external wall surfaces and a dedicated internal disinfecting unit for sterilizing the plastics material pre-forms on their internal wall surfaces, wherein the supply device comprises a heating path conveyor for conveying the plastics material pre-forms vertically oriented along the heating path to supply the plastics material pre-forms at least to the external disinfecting unit, wherein the heating path conveyor includes a plurality of rotatable holding elements, whereupon the plastics material pre-forms are arranged at least on the external disinfection device so as to be rotatable about their vertical axis during an external sterilization, wherein the sterilization device is incorporated only in part inside the heating device, wherein the plastics material pre-forms are held on the holding elements of the heating path conveyor and are supplied from the heating device to the sterilization device, and wherein the external disinfection unit is arranged inside the heating path and the internal disinfection unit is arranged outside the heating path and outside the heating device at an outlet of the heating device.

2. The apparatus according to claim 1, wherein the holding elements are arranged for holding the plastics material pre-forms on the inside, wherein the holding elements are capable of being arranged temporarily on the external disinfection device.

3. The apparatus according to claim 2, wherein the holding elements comprise mandrel-type holding elements.

4. The apparatus according to claim 1, wherein the external disinfection unit is arranged at the start of the heating path upstream of a heating element and downstream of an inlet of the heating device, between two heating elements inside the heating path or at the end of the heating path downstream of a heating element and upstream of a transfer device at the outlet and inside the heating device.

5. The apparatus according to claim 1, wherein the heating device comprises a device for generation of electrical charge particles for sterilizing the plastics material pre-forms.

6. The apparatus according to claim 1, wherein the heating device comprises at least in part a casing for screening out charge particles and/or X-ray radiation.

7. The apparatus according to claim 1, wherein the heating device comprises an additional clean room in which the sterilization device is arranged at least in part.

8. The apparatus according to claim 1, wherein an internal disinfection unit of the sterilization device is arranged outside the heating device, at a distance from an external disinfection unit of the sterilization device arranged inside the heating device, wherein both the internal disinfection unit and the external disinfection unit are arranged inside a common clean room under aseptic conditions.

9. An apparatus for processing plastics material containers comprising a shaping device for shaping plastics material pre-forms into plastics material containers, a heating device comprising a heating path for heating the plastics material pre-forms and with a sterilization device for the sterilization of the plastics material pre-forms, in which the apparatus comprises a supply device for supplying the plastics material pre-forms to the sterilization device, wherein the sterilization device comprises both a dedicated external disinfecting unit for sterilizing the plastics material pre-forms at least on their external wall surfaces and a dedicated internal disinfecting unit for sterilizing the plastics material pre-forms on their internal wall surfaces, wherein the supply device comprises a heating path conveyor for conveying the plastics material pre-forms vertically orientated along the heating path to supply the plastics material pre-forms at least to the external disinfecting unit, wherein the heating path conveyor includes a plurality of holding elements for holding the plastics material pre-forms on the inside, wherein the plastics material pre-forms are arranged on the holding elements so as to be rotatable about their vertical axis during an external sterilization, wherein the plastics material pre-forms are held on the holding elements of the heating path conveyor and are supplied from the heating device to the sterilization device, and wherein the holding elements are capable of being arranged temporarily on the external disinfection device.

10. The apparatus according to claim 9, wherein the holding elements comprise mandrel-type holding elements.

11. The apparatus according to claim 9, wherein the sterilization device is incorporated only in part inside the heating device, wherein the external disinfection unit is arranged inside the heating path and the internal disinfection unit is arranged outside the heating path.

12. The apparatus according to claim 9, wherein the external disinfection unit is arranged at the start of the heating path upstream of a heating element and downstream of an inlet of the heating device, between two heating elements inside the heating path or at the end of the heating path downstream of a heating element and upstream of a transfer device at the outlet and inside the heating device.

13. The apparatus according to claim 9, wherein the heating device comprises a device for generation of electrical charge particles for sterilizing the plastics material pre-forms.

14. The apparatus according to claim 9, wherein the heating device comprises at least in part a casing for screening out charge particles and/or X-ray radiation.

15. The apparatus according to claim 9, wherein the heating device comprises an additional clean room in which the sterilization device is arranged at least in part.

16. The apparatus according to claim 9, wherein an internal disinfection unit of the sterilization device is arranged outside the heating device, at a distance from an external disinfection unit of the sterilization device arranged inside the heating device, wherein both the internal disinfection unit and the external disinfection unit are arranged inside a common clean room under aseptic conditions.

17. An apparatus for processing plastics material containers comprising a shaping device for shaping plastics material pre-forms into plastics material containers, a heating device comprising a heating path for heating the plastics material pre-forms and with a sterilization device for the sterilization of the plastics material pre-forms, in which the apparatus comprises a supply device for supplying the plastics material pre-forms to the sterilization device, wherein the sterilization device comprises both a dedicated external disinfecting unit for sterilizing the plastics material pre-forms at least on their external wall surfaces and a dedicated internal disinfecting unit for sterilizing the plastics material pre-forms on their internal wall surfaces, wherein the supply device comprises a heating path conveyor for conveying the plastics material pre-forms vertically oriented along the heating path to supply the plastics material pre-forms at least to the external disinfecting unit, wherein the sterilization device comprises a device for generation of electrical charge particles for sterilizing the plastics material pre-forms, which stereilization device is incorporated in part inside the heating device, wherein the heating path conveyor includes a plurality of rotatable holding elements, wherein the plastics material pre-forms are held on the holding elements and are supplied from the heating device to the sterilization device, and wherein the external disinfection unit is arranged inside the heating path and the internal disinfection unit is arranged outside the heating path and outside the heating device at an outlet of the heating device.

18. The apparatus according to claim 17, wherein the holding elements are arranged for holding the plastics material pre-forms on the inside, wherein the holding elements are capable of being arranged temporarily on the external disinfection device.

19. The apparatus according to claim 18, wherein the holding elements comprise mandrel-type holding elements.

20. The apparatus according to claim 17, wherein the external disinfection unit is arranged at a start of the heating path upstream of a heating element and downstream of an inlet of the heating device, between two heating elements inside the heating path or at an end of the heating path downstream of a heating element and upstream of a transfer device at the outlet and inside the heating device.

21. The apparatus according to claim 17, wherein the heating device comprises at least in part a casing for screening out charge particles.

22. The apparatus according to claim 17, wherein the heating device comprises an additional clean room in which the sterilization device is arranged at least in part.

23. The apparatus according to claim 17, wherein an internal disinfection unit of the sterilization device is arranged outside the heating device, at a distance from an external disinfection unit of the sterilization device arranged inside the heating device, wherein both the internal disinfection unit and the external disinfection unit are arranged inside a common clean room under aseptic conditions.

24. The apparatus according to claim 17, wherein the heating path conveyor comprises a plurality of holding elements for holding the plastics material pre-forms on the inside.

25. The apparatus according to claim 24, wherein the sterilization device is incorporated in part inside the heating device, wherein the external disinfection unit is arranged inside the heating path and the internal disinfection unit is arranged outside the heating path.

26. The apparatus according to claim 24, wherein the holding elements are rotatable whereupon the plastics material pre-forms are arranged at least on the external disinfection device so as to be rotatable about a vertical axis during an external sterilization.

\* \* \* \* \*